(12) United States Patent
Orszulak (10) Patent No.: US 9,050,089 B2
(45) Date of Patent: Jun. 9, 2015

(54) ELECTROSURGICAL APPARATUS WITH TISSUE SITE SENSING AND FEEDBACK CONTROL

(75) Inventor: James H. Orszulak, Nederland, CO (US)

(73) Assignee: Covidien LP, Mansfield, MA (US)

( * ) Notice: Subject to any disclaimer, the term of this patent is extended or adjusted under 35 U.S.C. 154(b) by 952 days.

(21) Appl. No.: 13/118,973

(22) Filed: May 31, 2011

(65) Prior Publication Data

US 2012/0310241 A1 Dec. 6, 2012

(51) Int. Cl.
| | |
|---|---|
| A61B 18/14 | (2006.01) |
| A61B 18/12 | (2006.01) |
| A61B 17/00 | (2006.01) |
| A61B 18/00 | (2006.01) |
| H01B 7/04 | (2006.01) |

(52) U.S. Cl.
CPC .............. *A61B 18/12* (2013.01); *A61B 18/1206* (2013.01); *A61B 18/1445* (2013.01); *A61B 2017/00057* (2013.01); *A61B 2018/00178* (2013.01); *A61B 2018/0063* (2013.01); *A61B 2018/00642* (2013.01); *A61B 2018/00875* (2013.01); *H01B 7/048* (2013.01)

(58) Field of Classification Search
None
See application file for complete search history.

(56) References Cited

U.S. PATENT DOCUMENTS

| | | | |
|---|---|---|---|
| 3,588,689 A | * | 6/1971 | Crawford ...................... 324/526 |
| 3,895,635 A | | 7/1975 | Justus et al. |
| 4,413,304 A | | 11/1983 | Gerry |
| 5,693,045 A | | 12/1997 | Eggers |
| 5,831,210 A | | 11/1998 | Nugent |
| 5,836,946 A | * | 11/1998 | Diaz et al. ...................... 606/45 |
| 6,113,596 A | | 9/2000 | Hooven et al. |
| 6,190,385 B1 | | 2/2001 | Tom et al. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

Search Report from corresponding European Application No. 12170175.9 mailed Jan. 22, 2013.

(Continued)

*Primary Examiner* — Michael Peffley (57) ABSTRACT

An electrosurgical system and method for transmitting, monitoring, and controlling electrosurgical energy and tissue parameter quality at the tissue site. The electrosurgical system includes a generator adapted to generate electrosurgical energy for treating tissue. The generator includes one or more active output terminals which supply energy to the tissue. The active output terminals are operatively connected to one or more active leads. The generator also includes one or more return output terminal which returns energy from the tissue. The return output terminals are operatively connected to at least one return lead. The system also includes an electrosurgical instrument operatively connected to the one or more active leads and one or more return electrodes operatively connected to one or more return leads. The system further includes an electrosurgical cable including one or more active leads and one or more return leads. The one or more active leads and one or more return leads are wound in a double helix fashion such that the electrical field along the cable is mitigated along the length thereof.

15 Claims, 8 Drawing Sheets

(56) References Cited

U.S. PATENT DOCUMENTS

| | | | |
|---|---|---|---|
| 6,394,949 B1 | 5/2002 | Crowley et al. | |
| 6,689,131 B2* | 2/2004 | McClurken | 606/48 |
| 6,775,575 B2* | 8/2004 | Bommannan et al. | 607/101 |
| 7,057,111 B2 | 6/2006 | Fung et al. | |
| 7,090,673 B2 | 8/2006 | Dycus et al. | |
| D574,323 S | 8/2008 | Waaler | |
| 7,731,717 B2* | 6/2010 | Odom et al. | 606/51 |
| 7,819,865 B2 | 10/2010 | Orszulak | |
| 2003/0229344 A1 | 12/2003 | Dycus et al. | |
| 2004/0254573 A1 | 12/2004 | Dycus et al. | |
| 2005/0049454 A1 | 3/2005 | Ouchi | |
| 2008/0071261 A1* | 3/2008 | Orszulak | 606/34 |
| 2009/0254080 A1 | 10/2009 | Honda | |
| 2010/0094271 A1 | 4/2010 | Ward | |
| 2010/0217258 A1* | 8/2010 | Floume et al. | 606/34 |
| 2010/0319956 A1 | 12/2010 | Ballard et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 0619124 A1 | 10/1994 |
| EP | 0750886 A1 | 1/1997 |
| EP | 836868 | 4/1998 |
| EP | 882955 | 12/1998 |
| EP | 1051948 | 11/2000 |
| EP | 1201196 A1 | 5/2002 |
| EP | 1366724 | 1/2006 |
| EP | 880220 | 6/2006 |
| EP | 1776929 | 4/2007 |
| EP | 1820460 A2 | 8/2007 |
| EP | 1902681 A1 | 3/2008 |
| EP | 2156800 A1 | 2/2010 |
| EP | 2529687 A2 | 12/2012 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 2321193 A | 7/1998 |
| JP | 2001000444 A | 1/2001 |
| JP | 2001165612 A | 6/2001 |
| JP | 2008068364 A | 3/2008 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/048199 A1 | 5/2006 |
| WO | WO2006/050888 | 5/2006 |
| WO | WO2008/053532 | 5/2008 |
| WO | 2008102154 A2 | 8/2008 |
| WO | 2009018409 A2 | 2/2009 |

OTHER PUBLICATIONS

U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al., "Automatically Controlled Bipolar Electrosoagulation-'2COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No.6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.

(56) References Cited

OTHER PUBLICATIONS

Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
International Search Report EP07018517.8 dated Dec. 17, 2007.
European Search Report from Application No. EP13152674.1 dated Jun. 5, 2013.
European Search Report for EP 10 18 8338 dated Feb. 17, 2015.

* cited by examiner

ELECTROSURGICAL APPARATUS WITH TISSUE SITE SENSING AND FEEDBACK CONTROL

BACKGROUND

1. Technical Field

The present disclosure relates to an electrosurgical system and method for performing electrosurgical procedures. More particularly, the present disclosure relates to a system and method for transmitting and monitoring tissue and energy parameter information at the treatment site using sensor signal feedback from the treatment site. The present disclosure also relates to a system and method for transmitting, monitoring, and controlling electrosurgical radio frequency energy in a closed loop manner based on the tissue and energy parameters.

2. Background of Related Art

Electrosurgery involves application of high radio frequency electrical current to a surgical site to cut, ablate, or coagulate tissue. In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

Transmission of electrosurgical energy to the treatment site, namely from the electrosurgical generator to the instrument, is accomplished via an electrosurgical cable. During transmission an electrical field is generated through the cable and stray electrosurgical RF energy is typically emitted along the cable path, which tends to reduce treatment energy and generates RF noise. Moreover, the electrical fields may interfere with the operation of other electronic equipment in the surgical area, such as patient monitoring equipment.

SUMMARY

The present disclosure relates to transmission of electrosurgical radio frequency ("RF") energy. An electrosurgical cable is disclosed having close proximity electrical field coupling between a supply and return transmission leads. The coupling maximizes application of the RF energy delivered during surgery and minimizes the stray RF energy radiated by the supply and return leads. Close proximity electrical field coupling significantly reduces the electrical field via field cancellation thereby increasing patient and surgeon safety. Coupling provides a low loss inductive/capacitive ("LC") transmission medium via a three-dimensional geometric orientation of the supply and return leads. The geometric orientation affects LC reactive components and reduces uncontrolled capacitive reactance caused by stray RF radiation. In particular, capacitive reactance is caused by antenna effect (e.g., rapid discharge of stray RF energy) for transmission mediums shorter than half a wavelength. Therefore, loss of stray RF energy is contained to a predetermined level which also reduces capacitive loading to the energy source (e.g., electrosurgical energy).

The present disclosure provides an electrosurgical system including a generator having at least one active output terminal coupled to at least one active lead and at least one return output terminal coupled to at least one return lead and an electro surgical instrument coupled to the at least one active lead and the at least one return lead. The electrosurgical instrument includes at least one sensor disposed at a tissue contact portion and coupled to the generator through at least one sensor line. The system also includes an electro surgical cable including a dielectric core, wherein the at least one sensor line is disposed within the dielectric core and at least a portion of each of the at least one active lead and the at least one return lead are wound in a double helix about the dielectric core to minimize an electrical field generated by the at least one active lead and the at least one return lead.

In embodiments, the present disclosure also provides an electrosurgical system including a generator having at least one active output terminal coupled to at least one active lead and at least one return output terminal coupled to at least one return lead. The system includes an electrosurgical forceps having two jaw members, at least one of which is movable from a first position in spaced relation relative to the other to at least one subsequent position wherein the jaw members cooperate to grasp tissue therebetween, each of the jaw members including an electrically conductive sealing surface, wherein one electrically conductive sealing surface is coupled to the at least one active lead and another electrically conductive sealing surface is coupled to the at least one return lead. The forceps also include at least one sensor disposed within at least one of the jaw members and coupled to the generator through at least one sensor line. The system further includes an electrosurgical cable including a dielectric core, wherein the at least one sensor line is disposed within the dielectric core and at least a portion of each of the at least one active lead and the at least one return lead are wound in a double helix about the dielectric core to minimize an electrical field generated by the at least one active lead and the at least one return lead.

In further embodiments, the present disclosure provides an electrosurgical system including a generator having at least one active output terminal coupled to at least one active lead and at least one return output terminal coupled to at least one return lead. The system also includes an electrosurgical forceps having two jaw members, at least one of which is movable from a first position in spaced relation relative to the other to at least one subsequent position wherein the jaw members cooperate to grasp tissue therebetween. Each of the jaw members includes an electrically conductive sealing surface, wherein one electrically conductive sealing surface is coupled to the at least one active lead and another electrically conductive sealing surface is coupled to the at least one return lead. The forceps also include at least one electrical sensor disposed within at least one of the jaw members and coupled to at least one of the electrically conductive sealing surfaces and to the generator through at least one electrical sensor line and at least one optical sensor disposed within at least one of the jaw members and coupled to the generator through at least one optical transmission line. The system further includes an electrosurgical cable including a dielectric core, wherein the at least one sensor line is disposed within the dielectric core and at least a portion of each of the at least one active lead and the at least one return lead are wound in a double helix about the dielectric core to minimize an electrical field generated by the at least one active lead and the at least one return lead.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with bipolar electrosurgical systems and either an endoscopic instrument or an open instrument. It should also be appreciated that different electrical and mechanical connections and other considerations apply to each particular type of instrument.

The present disclosure provides for an electrosurgical transmission cable wound in a double helix having a proximal geometric relationship in three-dimensional physical space, to control the inductive and capacitive components of the transmission cable and significantly reduce the capacitive leakage due to RF radiation. The transmission cable according to present disclosure being wound in a double helix minimizes the stray RF radiation by reducing the transmitting antenna effect for transmission mediums shorter than ½ wavelength.

Figure 1:
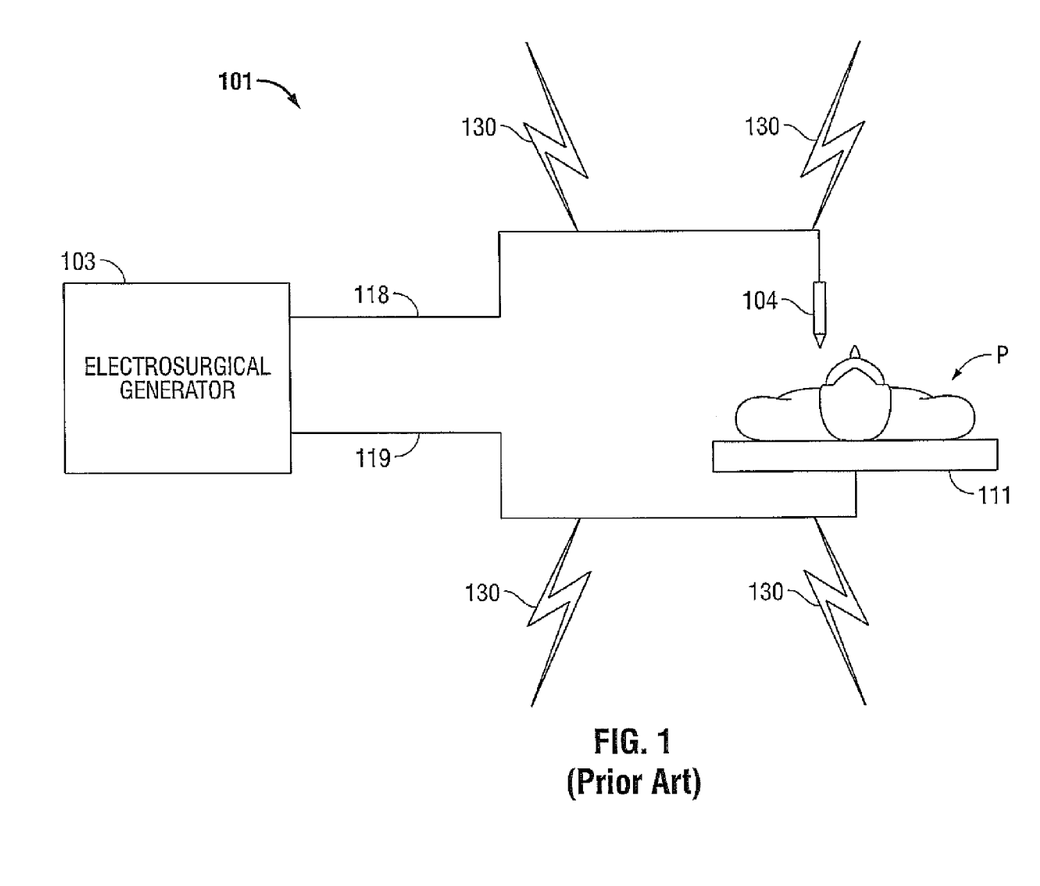
FIG. 1 is a schematic diagram of a prior art monopolar electrosurgical system.

FIG. 1 shows a prior art monopolar electrosurgical system 101. The system includes an electrosurgical generator 103 supplying electrosurgical radio frequency ("RF") energy to a monopolar electrosurgical instrument 104 via a supply transmission lead 118. The RF energy is returned to the generator 103 through a return electrode 111, shown as a return pad via a return transmission lead 119. Conventionally, the supply and return leads 118, 119 are oriented in a random fashion and thereby emit stray RF energy represented as radial emissions 130 due to RF energy flowing therethrough. In particular, random placement of the supply and return leads 118, 119 results in uncontrolled capacitive coupling due to stray RF radiation, RF radiation produces a transmitting antenna effect caused by random orientation of the supply and return leads 118, 119, which also generates an alternate RF leakage path for the transmitted RF energy.

Figure 2:
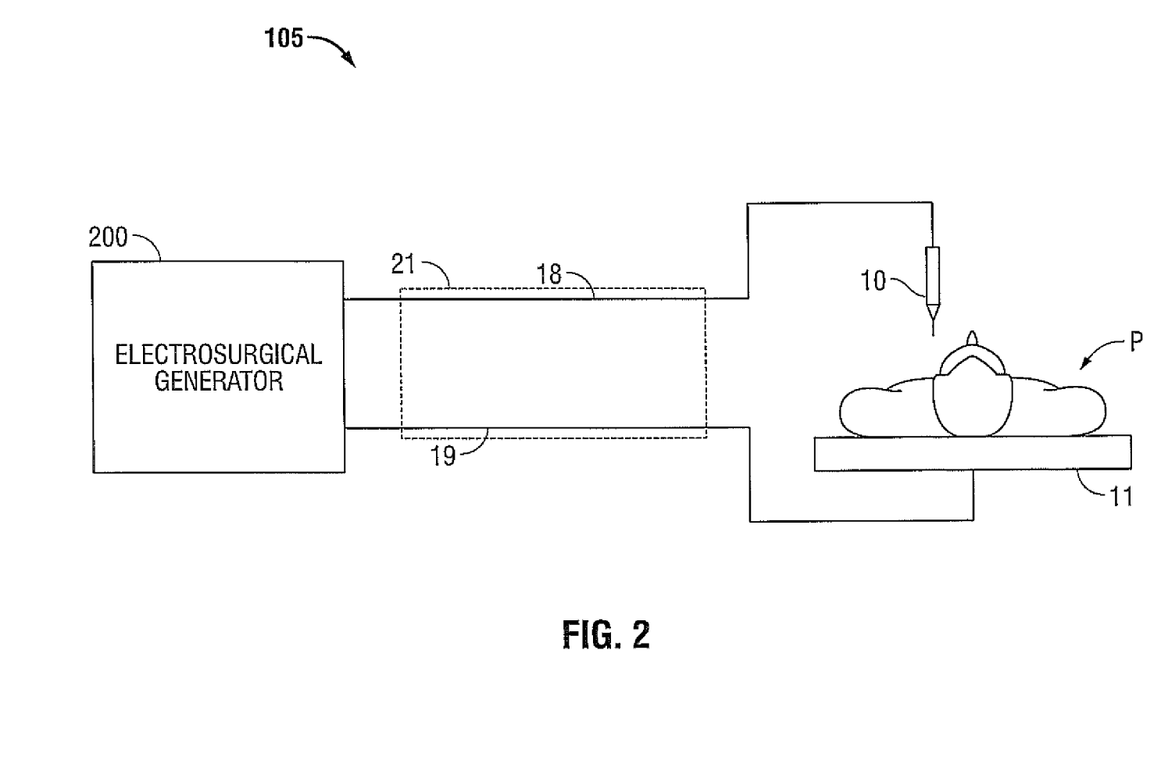
FIG. 2 is a schematic diagram of an embodiment of a monopolar electrosurgical system according to the present disclosure.
Figure 4:
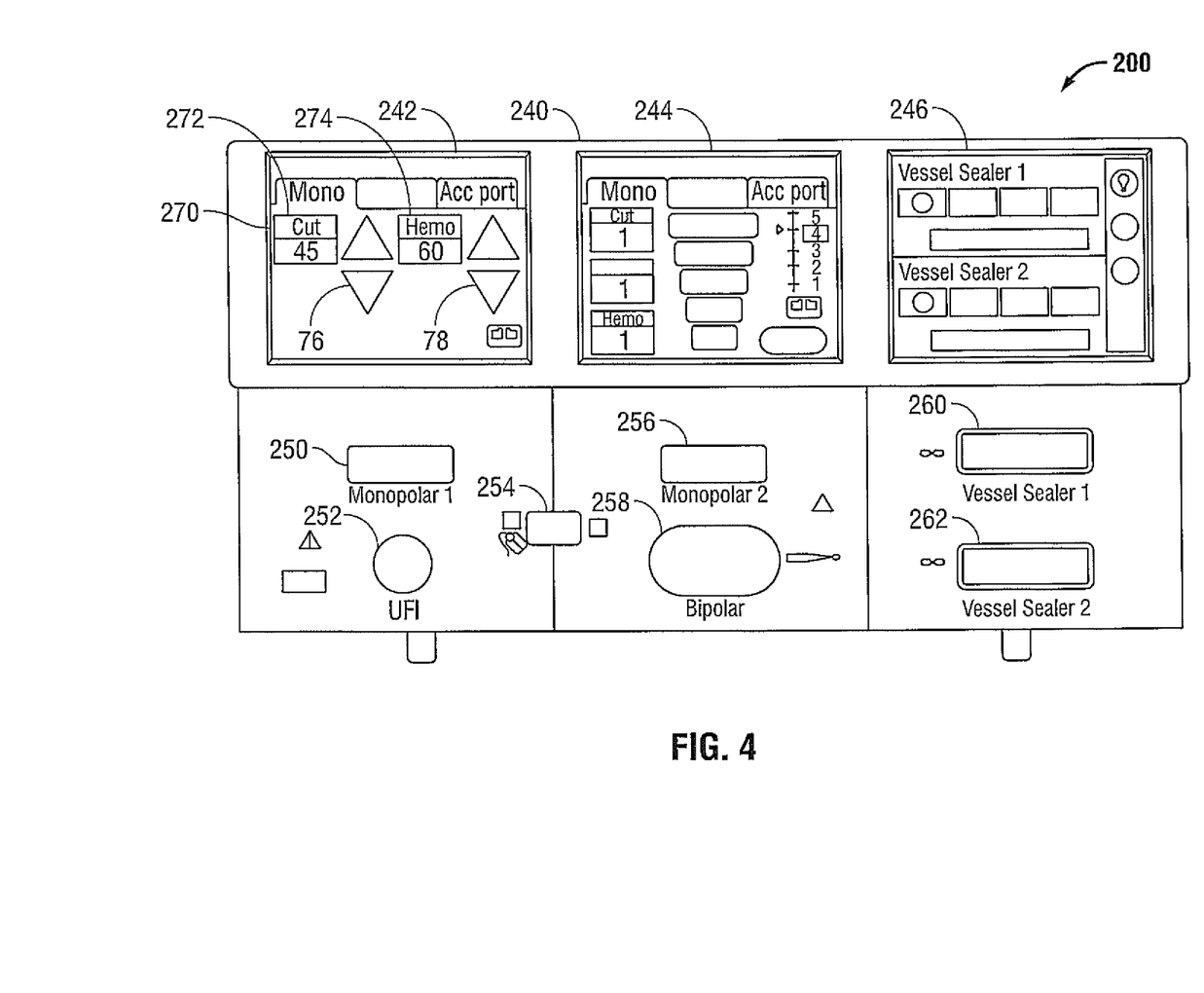
FIG. 4 is a front view of an electrosurgical generator according to the present disclosure.
Figure 5:
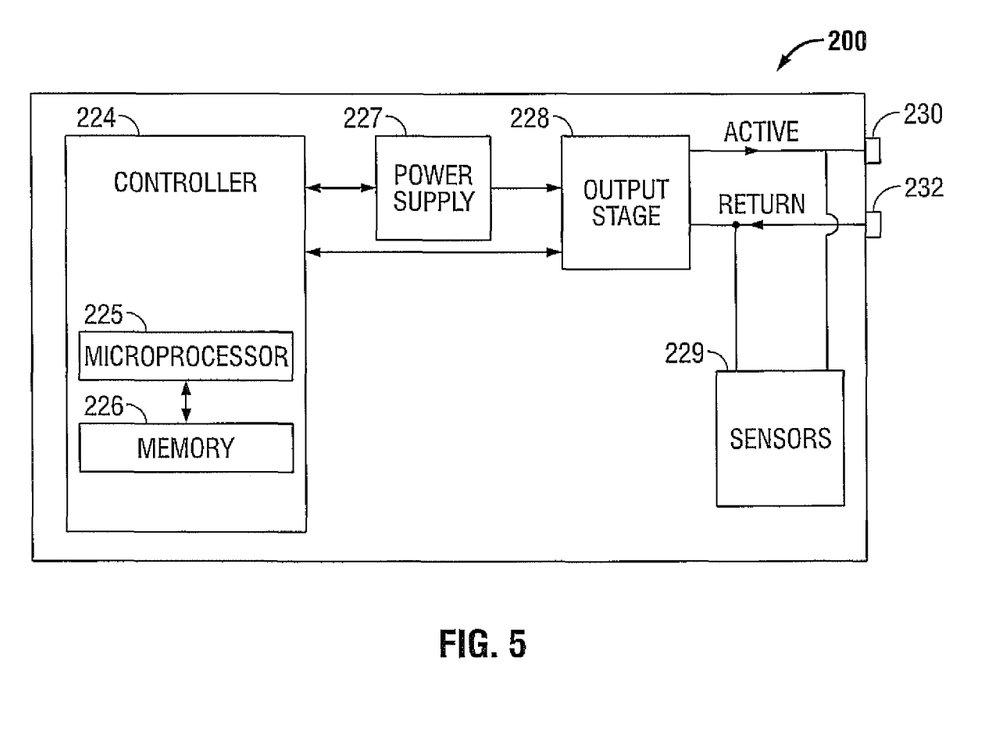
FIG. 5 is a schematic block diagram of the electrosurgical generator of FIG. 4 according to the present disclosure.

FIG. 2 shows an electrosurgical system 105 according to the present disclosure. The system is a monopolar electrosurgical system that includes an electrosurgical instrument 10 having one or more electrodes for treating tissue of a patient P. With reference to FIGS. 2, 4, and 5, electrosurgical RF energy is supplied to the instrument 10 by a generator 200 via a active lead 18, which is operatively connected to an active output terminal 230 (FIG. 5) of the generator 200, allowing the instrument 10 to coagulate, cut, ablate and/or otherwise treat tissue. The supply and return leads 18, 19 are enclosed within a cable 21. The electrosurgical instrument 10 may be coupled to the generator 200 at a connector 250 or 256 (FIG. 4), each of which is coupled to the active terminal 230.

Energy is returned to the generator 200 through a return electrode 11 and transmitted through a return lead 19, which is operatively connected to a return output terminal 232 (FIG. 5) of the generator 200. The system 105 may include a plurality of return electrodes 11 that are disposed on a patient to minimize the chances of tissue damage by maximizing the overall contact area with the patient. The return electrode 11 may be coupled to the generator 200 at a connector 254 (FIG. 4), which is coupled to the return terminal 232. In embodiments, the generator 200 and the return electrode 11 may be configured for monitoring so-called "tissue-to-patient" contact to insure that sufficient contact exists therebetween to further minimize chances of tissue damage. The generator 200 may include a plurality of supply and return terminals and corresponding number of transmission cables (e.g., two of each).

Figure 3:
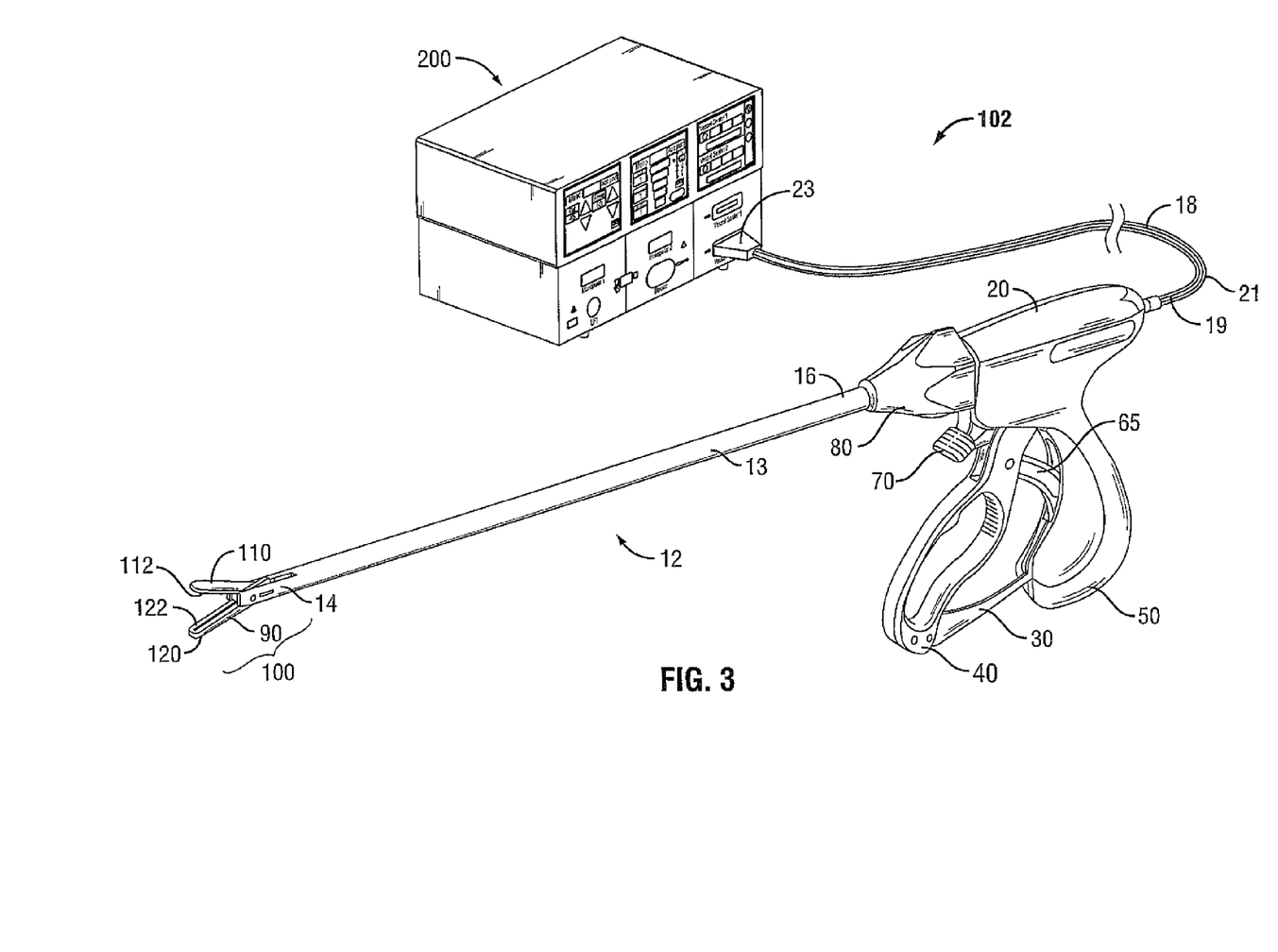
FIG. 3 is a perspective view of an embodiment of a bipolar electrosurgical system according to the present disclosure.

FIG. 3 shows a bipolar electrosurgical system 102 according to the present disclosure. The system 102 is a bipolar electrosurgical system that includes an electrosurgical forceps 12 having opposing jaw members. The forceps 12 is shown as an endoscopic version of a vessel sealing bipolar forceps. In embodiments, the forceps 12 may be any suitable electrosurgical sealing instrument, such as open-type forceps. The forceps 12 also includes a housing 20, a handle assembly 30, a rotating assembly 80, and a trigger assembly 70 which mutually cooperate with the end effector assembly 100 to grasp, seal and, if required, divide tissue. Forceps 12 includes a shaft 13 having a distal end 14 that mechanically engages the end effector assembly 100 and a proximal end 16 that mechanically engages the housing 20 proximate the rotating assembly 80. The end effector assembly 100 includes two jaw members 110, 120 movable from a first position wherein the jaw members are spaced relative to on another to a closed position wherein the jaw members 110 and 120 cooperate to grasp tissue therebetween. Each of the jaw members includes an electrically conductive sealing surface 112 and 122, respectively, connected to an energy source (e.g., a generator 200). The electrically conductive sealing surfaces 112 and 122 communicate electrosurgical energy through the tissue held therebetween. Electrosurgical RF energy is supplied to the forceps 12 by generator 200 via the active lead 18 operatively connected to the active electrode (e.g., sealing surface 112) and returned through the return lead 19 operatively connected to the return electrode (e.g., sealing surfaces 122).

Handle assembly 30 includes a fixed handle 50 and a movable handle 40. Handle 40 moves relative to the fixed handle 50 to actuate the end effector assembly 100 and enable a user to selectively grasp and manipulate tissue. The jaw members 110 and 120 move in response to movement of handle 40 from an open position to a closed position. In the open position, the sealing surfaces 112 and 122 are disposed in spaced relation relative to one another. In a clamping or closed position, the sealing surfaces 112 and 122 cooperate to grasp tissue and apply electrosurgical energy thereto. Jaw members 110 and 120 are activated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/369,894 entitled "Vessel Sealer And Divider And Method Manufacturing Same" and commonly owned U.S. application Ser. No. 10/460,926 entitled "Vessel Sealer And Divider For Use With Small Trocars And Cannulas."

The forceps 12 also includes a plug 23 that connects the forceps 12 to a source of electrosurgical energy, e.g., generator 200, via cable 21. With reference to FIGS. 3-5, the electrically conductive sealing surfaces 112 and 122 are connected to the generator 200 through cable 21 that includes the supply and return leads 18, 19 coupled to the active and return terminals 230, 232 (FIG. 5), respectively. The electrosurgical forceps 12 is coupled to the generator 200 via the plug 23 at a connector 260 or 262 (FIG. 4), each of which is coupled to the active and return terminals 230 and 232 (e.g., pins, etc.).

With reference to FIGS. 4 and 5, front face 240 of the generator 200 is shown. The generator 200 may be any suitable electrosurgical generator and may include a plurality of connectors 250-262 to accommodate various types of electrosurgical instruments (e.g., electrosurgical forceps 12, etc.). The connectors 250-262 may include various detection devices that can read identifying information encoded on the plugs of the instruments (e.g., plug 23 of the forceps 12). The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-volatile memory, etc., which may then be coupled to or integrates into the plug. Corresponding detection devices may include, but are not limited to, bar code readers, electrical sensors, RFID readers, Hall Effect sensors, memory readers, etc. and any other suitable decoders configured to decode data encoded on the plug.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 12, etc.). The user then makes inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 12 that may be plugged into the connectors 260 and 262. The generator 200 outputs energy through the connectors 260 and 262 suitable for sealing tissue grasped by the forceps 12. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 12 being utilized, such that various instruments provide the user with a specific intensity scale corresponding to the forceps 12.

FIG. 5 shows a schematic block diagram of the generator 200 configured to output electrosurgical energy. The generator 200 includes a controller 224, a power supply 227, and an output stage 228. The power supply 227 may be a direct current high voltage power supply and is connected to an AC source (e.g., electrical wall outlet) and provides high voltage DC power to an output stage 228, which then converts high voltage DC power into treatment energy (e.g., ultrasonic, electrosurgical or microwave) and delivers the energy to the active terminal 2230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may include transitory type memory (e.g., RAM) and/or non-transitory type memory (e.g., flash media, disk media, etc.). The microprocessor 225 includes an output port that is operably connected to the power supply 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200 or forceps 12. The controller 224 utilizes the input signals to adjust power outputted by the generator 200 and/or performs other control functions thereon.

Figure 6:
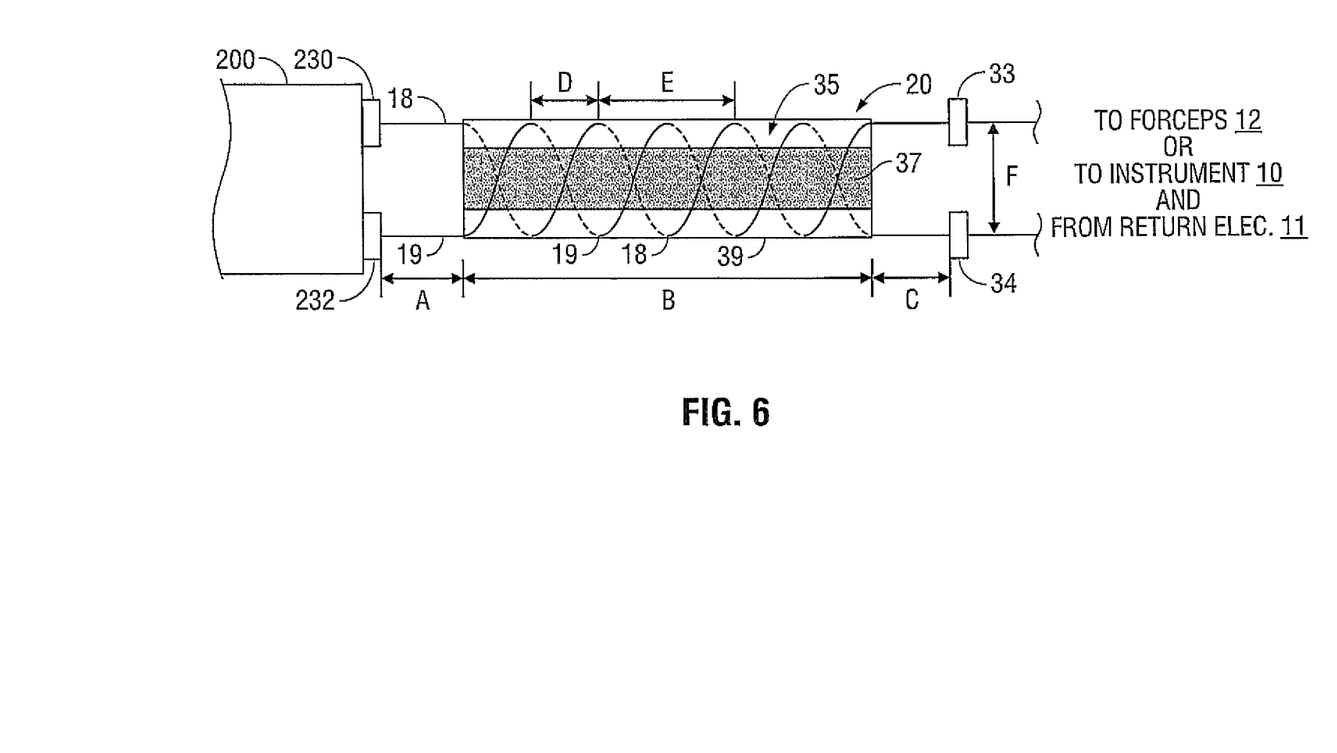
FIG. 6 is a cross-sectional schematic view of an electrosurgical cable according to the present disclosure.

FIG. 6 shows a cross-sectional view of the cable 21. Cable 21 includes the supply and return leads 18, 19 operatively connected to the generator 200 via active and return terminals 230, 232 respectively. Supply and return leads 18, 19 may be insulated. Various types of insulating materials may be used, which are within the purview of those skilled in the art. The supply and return leads 18, 19 extend from the active and return terminals 230, 232 respectively for a distance A, which is optimally controlled by the location of active and return terminals 230, 232 and may be from about 0.1 inches to about 6 inches. Leads 18, 19 are then helix-wound in a wound portion 35, which may be from about 0.1 inch to about 20 feet, depending upon a desired cable inductance and capacitance. Alternatively, the wound portion 35 may extend from the active and return terminals 230, 232 without extending the supply and return leads 18, 19 for the distance A.

The wound portion 35, along cable length B, can be of any length depending on geometric configuration and physical properties (e.g., tensile strength, flexibility, etc.) of materials used in manufacturing of cable components. More specifically, leads 18, 19 are oriented in a double helix which includes two congruent helixes with the same axis, differing by a translation along the axis. The leads 18, 19 may be oriented in a plurality of other arrangements which wrap the leads 18, 19 around themselves. The arrangement of the leads 18, 19 in a double helix orients the opposing electrical fields generated by the electrosurgical RF energy passing therethrough to mitigate and/or cancel out thereby minimizing the amount of lost stray electrical RF energy.

The distance D of the portion 35, represents the distance between one apex of one helix and a nearest apex of another helix, and may be about ½ inch. The distance E, which is the distance between two apexes of the same helix may be about 1 inch. The outer diameter F of the cable 21 may vary or be about ⅜ of an inch, depending upon a desired cable inductance, capacitance or electrical field minimization.

Leads 18, 19 are wound within the cable 21 around a dielectric core 37, which provides support for the leads 18, 19, an insulative sheath 39 covers the leads 18, 19. The dielectric core 37 may have a substantially tubular shape with an air core surrounded by a low dielectric constant material. The sheath 39 may be of the same type dielectric material as the dielectric core 37. Leads 18, 19 may include wire or conductive trace and may have an inductance rating of about 7.37 µH at about 473 kHz and capacitance of about 32.0 PF at about 1 MHz to yield a cable-self-resonance of about 10.4 MHz.

Cable 21 as illustrated in FIG. 6, provides a transmission medium to deliver RF energy from the generator 200 to a tissue site. Cable 21 represents one embodiment for the RF transmission medium, which reduces the radiated RF electrical field and maximizes the applied clinical treatment energy delivered to the tissue site. The dimensions A, B, C, D, E and F of FIG. 6 form a unique proximal geometric relationship in three dimensional space to control the electrical field coupling between the active and return output terminals of the generator 200 to significantly reduce the Volts per meter and Amps per meter electrical field radiation by field cancellation.

The physical dimensions A, B, C, D, E and F are interdependent and may be optimized to provide a low loss inductive and capacitive transmission medium, which in addition to controlling the electrical field, reduces uncontrolled capacitive coupling caused by stray RF radiation. In particular the following formulas (I) and (II) illustrate the interdependent relationship of dimensions A, B, C, D, E and F with respect to inductive and capacitive properties of the cable 21.

$$\text{Inductance} = B(10.16 \times 10^{-9}) \text{Ln}\,[(2 \times D)/d)] + 2(A+C) \quad (\mu\text{H/in. for specified wire}) \qquad (I)$$

$$\text{Capacitance} = [(B \times (0.7065 \times 10^{-12}))/\text{Ln}\,[(2 \times D)/d]]er \qquad (II)$$

In formulas (I) and (II) "d" denotes diameter of the wire (e.g., supply and return leads 18, 19), "er" denotes the dielectric constant of the insulator. Further, E=2×D, the ratio of E to D establishes a continuum of the helix configuration and F=k× D, where "k" is a constant from about 0.5 to about 1.5.

At the distal end of the portion 35, the leads 18, 19 are unwound and are operatively connected to device connectors 33, 34 respectively, which may be pins disposed within the forceps 12. Leads 18, 19 extend a distance C from the portion 35 to the connectors 33, 34 in an unwound state length dependant on the instrument application.

In bipolar electrosurgery, the connectors 33, 34 may be situated on the forceps 12. In monopolar surgery, the connector 33 is operatively connected to the instrument 10 and the connector 34 is connected to the return electrode 11. As discussed above, in situations where a plurality of return electrodes are used, the return lead 19 may split into corresponding number of leads to operatively connect all of the return electrodes 11 to the generator 200. In monopolar surgery the length C for leads 18 and 19 may be of equal or different lengths to accommodate manipulation of surgical instrument in the operating site.

Cable 21 according to the present disclosure orients the supply and return leads 18, 19 so that the electrical fields generated therethrough are canceled, thereby reducing the amount of leaked stray RF energy. More specifically, placement and orientation of the leads 18, 19 in the manner discussed above provides for close proximity of electrical fields generated during transmission of electrosurgical RF energy and maximizes amount of energy delivered to the treatment site. Reducing the electrical fields also increases safety of operating room personnel and the patient.

Reduced RF radiation decreases capacitive and RF field leakage and improves RF control of the delivered energy. Reduced RF radiation also decreases RF transmission loss and improves efficiency of the generator 200 by reducing RF harmonic component, minimizing corruption of the RF source and reducing peripheral conductive and radiative emissions. Further, reducing RF radiation also decreases the RF noise to additional equipment found in the operating room, such as patient monitoring equipment.

In addition, the transmission system according to the present disclosure also provides novel ways to sense tissue and energy parameters directly at the tissue site. Conventional electrosurgical systems sense and control energy delivery at the power source and calibrate for the energy loss during transmission to the tissue site. In particular, energy lost during transmission to and from the instrument as well as internal loss within the power source is compensated in a less than optimal method. Thus, conventional electrosurgical system do not directly control energy applied to the tissue or monitor energy and tissue parameters at the tissue site, which may result in less than optimal tissue treatment.

The present disclosure provides a system for sensing tissue and energy parameters directly at the tissue site allowing for accurate feedback control of the applied energy to optimally achieve desired tissue treatment effect including, but not limited to, hemostasis, vessel sealing, and coagulation. In particular, the present disclosure includes sensors disposed at the treatment site for sensing various tissue and energy parameters and utilizes the transmission medium (e.g., cable 21) to minimize the voltage and current electromagnetic field components and maximize the sensed signal integrity. The sensed signals are then transmitted to the power source through the transmission medium with minimal or negligible loss or signal degradation conventional to conventional losses described above. A transmission medium cable for transmitting electrosurgical energy from a generator to an instrument is disclosed in a commonly-owned U.S. Pat. No. 7,819,865, entitled "Electrosurgical Radio Frequency Energy Transmission Medium," the entire contents of which is incorporated by reference herein.

Figure 7:
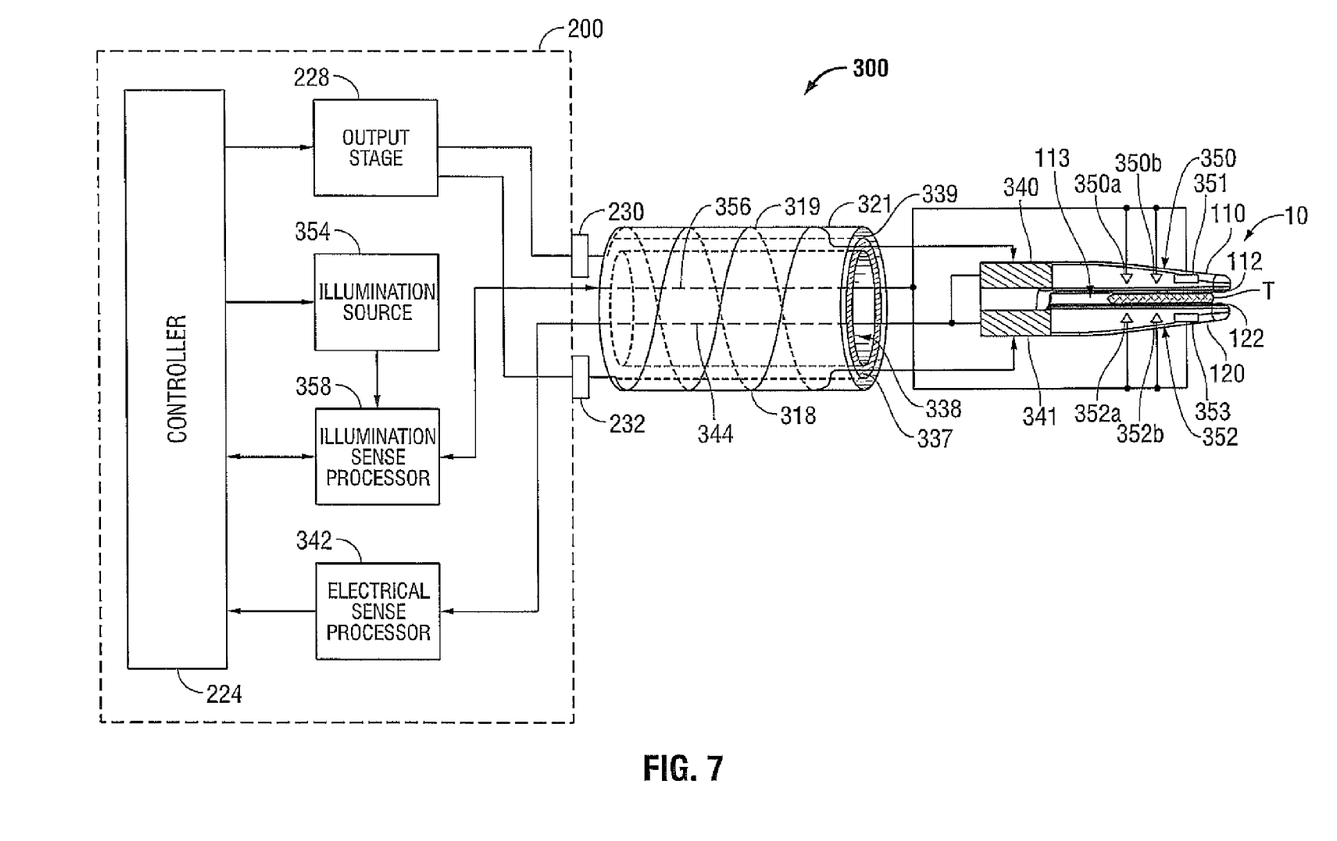
FIG. 7 is a cross-sectional schematic view of an electrosurgical system including an electrosurgical cable according to the present disclosure.
Figure 8:
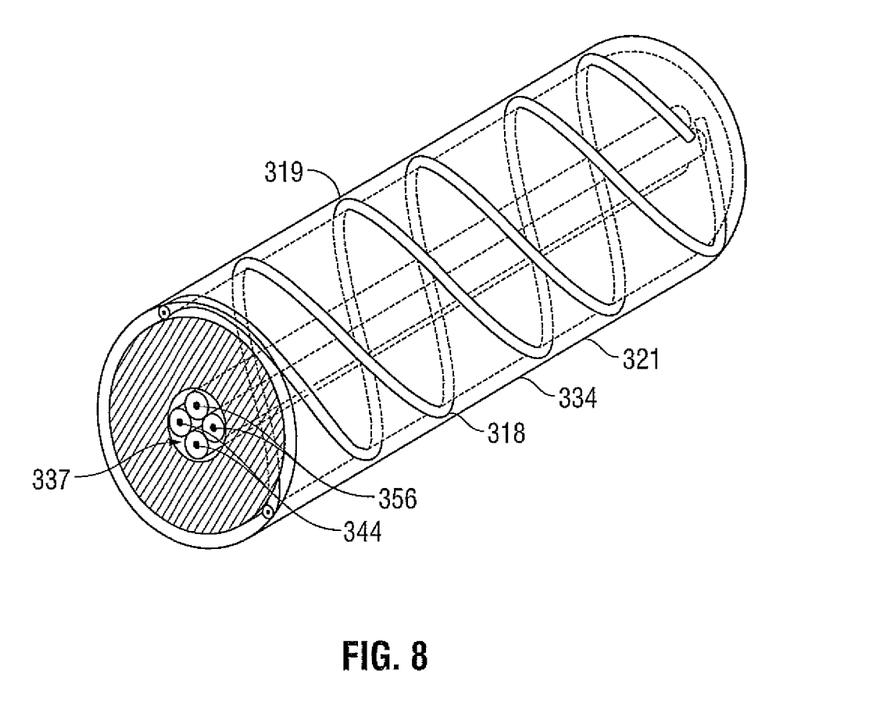
FIG. 8 is a cross-sectional perspective view of the electrosurgical cable of FIG. 7 according to the present disclosure.

FIG. 7 shows a system 300 including generator 200 and forceps 10, shown schematically as a pair of opposing jaw members 110 and 120 each having electrically conductive sealing surfaces 112 and 122. System 300 provides control of the treatment energy (e.g., output of the generator 200) in a closed loop manner based on the tissue and energy properties sensed directly at the tissue site, T. Parameters of the treatment energy which may be adjusted by the system 300 include, but are not limited to, energy, power, voltage, current, tissue impedance, and parameter time, rates of change of these parameters, and combinations thereof. Measured tissue and energy properties include, but are not limited to, tissue impedance, tissue translucency/opacity, tissue hydrology, tissue, vascularity, burst strength of sealed vessels, tissue seal fusion, temperature, depth of tissue penetration with applied treatment energy, thermal spread, and combinations thereof. The system 300 includes optical and electrical sensors for detecting tissue and energy properties directly at the tissue site and transmitting the sensor measurements along electrical and/or optical cables to the generator 200. With reference to FIGS. 7 and 8, the cables (e.g., optical transmission lines 356 and/or electrical sensor lines 344) are disposed within a transmission medium of wound RF supply and return leads 318, 319 to minimize tissue site sensor signal degradation and allow multi-sensor communication of tissue sensory devices. In particular, the transmission medium allows for use of optical fibers, which enable transmissive, reflective, spectral and visual analysis of tissue.

Forceps 10 is coupled to the generator via the cable 321. Generator 200 includes the output stage 228 coupled to supply and return leads 318, 319 disposed within the cable 321. The supply and return leads 318, 319 are operatively connected to the generator 200 via active and return terminals 230, 232 respectively. The cable 321 is substantially similar to cable 21 described above with respect to FIG. 6 above, thus the embodiment of cable 21 is incorporated into the embodiment of cable 321 including, but not limited to, the elements of the cable 21, such as leads 18, 19, dielectric core 37, insulative sheath 39, and the like, as well as configuration, arrangement, and material properties of these components.

Cable 321 includes a dielectric core 337 forming the core of cable 321. Supply and return leads 318 and 319 are wound about dielectic core 337 in a double helix manner and arranged in similar configuration as leads 18 and 19 of FIG. 6. Dielectric core 337 has a substantially tubular structure having a lumen 338 defined therethrough. The arrangement of the leads 318, 319 in a double helix orients the opposing electrical fields generated by the electrosurgical RF energy passing therethrough to mitigate and/or cancel out thereby minimizing the amount of lost stray electrical RF energy. Cable 321 also includes an insulative sheath 339 which is disposed over leads 318 and 319 thereby securing the leads 318 and 319 to the dielectic core 337.

Cable 321 as illustrated in FIG. 7, provides a transmission medium to deliver RF energy from the generator 200 to the tissue T grasped between the jaw members 110 and 120. Forceps 10 includes one or more electrical sensors 340 and 341 connected between supply and return leads 318 and 319. The electrical sensors 340 and 341 are disposed at the tissue contact portion 113, namely at the jaw members 110 and 120. Electrical sensors 340 and 341 may be any suitable electrical sense transducer including, but not limited to, conductive resistors, sense transformers, thermal impedance devices, composite materials having known resistivity and thermal impedance, and combination thereof. Electrical sensors 340 and 341 may be disposed in one or both of the jaw members 110 and 120 and are in electrical communication with the electrically conductive sealing surfaces 112 and 122, respectively. This configuration allows the electrical sensors 340 and 341 to detect tissue impedance, power, voltage, current, resistance, phase, temperature, time parameter rates of change thereof (e.g., as calculated by the controller 224), and combinations thereof. The electrical sensors 340 and 341 measure these properties passing directly through the electrically conductive sealing surfaces 112 and 122 without measuring the energy sensory information at the generator 200 as performed in conventional electrosurgical systems. Electrical sensors 340 and 341 may measure the above-described sensory information and other electrical properties of the electrosurgical energy delivered to the tissue T through electrically conductive sealing surfaces 112 and 122. The measured parameters may then be used to determine various tissue and energy properties described above.

Electrical sensors 340 and 341 are coupled to an electrical sense processor 342 via one or more electrical sensor lines 344. As shown in FIG. 8, the lines 344 are disposed within the cable 321 and pass through the lumen 338. The lines 344 may be insulated. Various types of insulating materials may be used, which are within the purview of those skilled in the art. Sense processor 342 is disposed within the generator 200 and is coupled to the controller 224. Sense processor 342 receives the electrical sense signals from the electrical sensors 340 and 341 and determines tissue and/or energy parameters at the tissue T and then transmits the processed sense signals to the controller 224. In embodiments, the electrical sensors 340 and 341 may be coupled to the controller 224 (e.g., isolated) such that the controller 224 performs the functionality of the sense processor 342, namely, determination of tissue and energy parameters based on electrical sense signals.

Forceps 10 also includes one or more optical sensor arrays 350 and 352 at the tissue contact portion 113 disposed within the jaw members 110 and 120, respectively. The sensor arrays 350 and 352 may be disposed in direct contact or non-contact configuration (e.g., separated by the sealing plates 112 and 122) with the tissue T. Each array 350 and 352 may include a plurality of optical sensors 350a, 350b and 352a, 352b, respectively. Suitable optical sensors include, but are not limited to, optical detectors that are quantum devices in which an individual photon produces a discrete effect, photoresistors or light-dependent resistors in which resistance is a function of light intensity, photodiodes operating in a photovoltaic mode or in a photoconductive mode, photovoltaic cells producing a voltage and an electric current when illuminated, photosensor cells containing a photocathode, light-emitting devices (LEDs) that are reverse-biased to act as photodiodes, phototransistors that function as amplifying photodiodes, optical detectors that function as thermometers converting heat of incoming radiation to an electrical current, and the like.

Each array 350 and 352 also includes one or more optical transmitters 351 and 353. Suitable optical transmitters include, but not limited to, light-emitting electronic devices such as a light-emitting diodes (LED), or electrical cables that transmit electrical signals that provide optical information from a light source. In embodiments, the optical transmitters 351 and 353 may also function alternately as optical sensors 350a, 350b and 352a, 352b to serve as a dual-function optical transmitter and optical receiver. In further embodiments, a dual-function optical transmitter and optical receiver may include a multiplexer device.

In embodiments, optical sensors 350a, 350b and 352a, 352b and optical transmitters 351 and 353 are in optical communication with the tissue T. This may be accomplished by including a transparent opening for each of the optical sensors 350a, 350b and 352a, 352b and the optical transmitters 351 and 353. In embodiments, the optical sensors 350a, 350b and 352a, 352b and the optical transmitters 351 and 353 may be coupled to the openings via optical transmission media, which include, but are not limited to, small diameter optical fibers, incorporating Bragg gratings that phase correlate the tissue T properties by light propagating therethrough in either transmissive or reflective mode.

The optical sensors 350a, 350b and 352a, 352b and optical transmitters 351 and 353 may be configured for transmissive, reflective, spectral and visual analysis of tissue. In transmissive analysis, the optical sensors 350a and 350b detect light transmission through the tissue T by the optical transmitter 353 and the optical sensors 352a and 352b detect light transmission through the tissue T by the optical transmitter 351. In reflective analysis, the optical sensors 350a and 350b detect light reflected off the tissue T, The optical sensors 352a and 352b detect light reflected off the tissue T. In spectral analysis, the optical sensors 350a, 350b and 352a, 352b may detect the light emitted by either of the optical transmitters 351 and 353. In visual analysis, the optical sensors 350a, 350b and 352a, 352b may be any image sensor, such as a complementary metal-oxide semiconductor ("CMOS") or a charge-coupe device ("CCD") sensor that is coupled to an image output device (e.g., monitor).

The optical sensors 350a, 350b and 352a, 352b and the optical transmitters 351 and 353 are coupled to an illumination source 354 and an illumination sense processor 358 via one or more optical transmission lines 356 as shown in FIGS. 7 and 8. Suitable optical transmission lines 356 include optical fibers as described above with respect to optical sensors or an electrically conductive cable capable of providing optical communication between the optical sensors 350a, 350b and 352a, 352b and the illumination source 354.

The illumination source 354 supplies light to the tissue T through the optical transmitters 351 and 353. Light propagating through the tissue T is detected by the optical sensors 350a, 350b and 352a, 352b and convert the photonic signal to an electrical signal that is then transmitted to the sense processor 358. The sense processor 358 is configured to sense changes in light trough the tissue T in response to tissue treatment and communicate such changes to the controller 224 to determine tissue properties including, but not limited, to transmittance, reflectance, translucency, opacity, hydrology, vascularity, thermal spread, tissue treatment depth, tissue seal quality, temperature, spectral content, and combinations thereof. In embodiments, the optical sensors 350a, 350b and 352a, 352b and the optical transmitters 351 and 353 may be directly coupled to the controller 224 such that the controller 224 performs the functionality of the sense processor 358, namely, determination of tissue and energy parameters based on optical sense signals.

In response to the electrical and optical sense signals, the controller 224 may adjust the output of the generator 200. In embodiments, the controller 224 may include one or more algorithms for controlling the output as a function of the detected tissue and/or energy properties. In particular, the algorithm implemented in the controller 224 may drive the output of the generator 200 as well as its components, including the illumination source 354, the illumination sense processor 358, and the electrical sense processor 342 to continuously monitor tissue and/or energy properties for adjustment of the generator output.

A system and method for monitoring tissue during electrosurgical application via optical sensors is disclosed in a commonly-owned U.S. patent application Ser. No. 12/249,263, entitled "Apparatus, System And Method For Monitoring Tissue During An Electrosurgical Procedure," the entire contents of which is incorporated by reference herein.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
  a generator including:
    an illumination source;
    an illumination sense processor;
    at least one active output terminal coupled to at least one active lead; and
    at least one return output terminal coupled to at least one return lead;
  an electrosurgical instrument including first and second jaw members configured to grasp tissue, the first jaw member coupled to the at least one active lead and including an optical transmitter configured to transmit a light through the tissue, and the second jaw member coupled to the at least one return lead and including an optical receiver configured to detect the light transmitted through the tissue; and
  an electrosurgical cable including:
    a dielectric core;
    a first sensor line coupling the optical transmitter to the illumination source; and
    a second sensor line coupling the optical receiver to the illumination sense processor, the second sensor line including at least one phase-correlated Bragg grating, wherein the first and second sensor lines are disposed within the dielectric core and at least a portion of each of the at least one active lead and the at least one return lead are wound in a double helix about the dielectric core.

2. The electrosurgical system according to claim 1, wherein the at least one active lead and the at least one return lead are enclosed by a sheath.

3. The electrosurgical system according to claim 1, wherein the electrosurgical instrument includes at least one electrical sensor.

4. The electrosurgical system according to claim 3, wherein the at least one electrical sensor is selected from the group consisting of conductive resistors, sense transformers, thermal impedance devices, composite materials, and combinations thereof.

5. An electrosurgical system, comprising:
   a generator including:
      an illumination source;
      an illumination sense processor;
      at least one active output terminal coupled to at least one active lead; and
      at least one return output terminal coupled to at least one return lead;
   an electrosurgical forceps including:
      two jaw members, at least one of which is movable from a first position in spaced relation relative to the other to at least one subsequent position wherein the jaw members cooperate to grasp tissue therebetween, one of the jaw members including at least one optical transmitter configured to transmit a light through the tissue and the other jaw member including at least one optical receiver configured to detect the light transmitted through the tissue, each of the jaw members including an electrically conductive sealing surface, wherein one electrically conductive sealing surface is coupled to the at least one active lead and another electrically conductive sealing surface is coupled to the at least one return lead; and
   an electrosurgical cable including:
      a dielectric core;
      a first sensor line coupling the at least one optical transmitter to the illumination source;
      a second sensor line coupling the at least one optical receiver to the illumination sense processor, the second sensor line including at least one phase-correlated Bragg grating, wherein the first and second sensor lines are disposed within the dielectric core and at least a portion of each of the at least one active lead and the at least one return lead are wound in a double helix about the dielectric core.

6. The system according to claim 5, wherein the at least one optical receiver and the at least one optical transmitter are configured to measure at least one property of the tissue selected from the group consisting of transmittance, reflectance, translucency, opacity, hydrology, vascularity, thermal spread, tissue treatment depth, seal quality, spectral content, and combinations thereof.

7. The system according to claim 5, wherein the at least one optical receiver is an image sensor.

8. The system according to claim 5, wherein the at least one optical receiver is selected from the group consisting of a photoresistor, a photodiode, a photovoltaic cell, a phototube, a reverse-biased light-emitting device, and a phototransistor.

9. The system according to claim 5, wherein the first and second sensor lines are optical fibers.

10. The system according to claim 9, wherein each of the optical fibers includes at least one Bragg grating.

11. An electrosurgical system, comprising:
    a generator including:
       an illumination source;
       an illumination sense processor;
       at least one active output terminal coupled to at least one active lead; and
       at least one return output terminal coupled to at least one return lead;
    an electrosurgical forceps including:
       first and second jaw members, at least one of which is movable from a first position in spaced relation relative to the other to at least one subsequent position wherein the jaw members cooperate to grasp tissue therebetween, each of the first and second jaw members including an electrically conductive sealing surface, wherein one electrically conductive sealing surface is coupled to the at least one active lead and another electrically conductive sealing surface is coupled to the at least one return lead;
       at least one electrical sensor disposed within at least one of the first and second jaw members and coupled to at least one of the electrically conductive sealing surfaces;
       at least one optical transmitter disposed within the first jaw member, the at least one optical transmitter configured to transmit a light through the tissue;
       at least one optical sensor disposed within the second jaw member, the at least one optical sensor configured to detect the light transmitted through the tissue; and
    an electrosurgical cable including:
       a dielectric core;
       at least one electrical sensor line coupling the at least one electrical sensor to the generator;
       a first optical transmission line coupling the at least one optical transmitter to the illumination source; and
       a second optical transmission line coupling the at least one optical receiver to the illumination sense processor, the second optical transmission line including at least one phase-correlated Bragg grating,
       wherein the at least one sensor line and the first and second optical transmission lines are disposed within the dielectric core and at least a portion of each of the at least one active lead and the at least one return lead are wound in a double helix about the dielectric core.

12. The electrosurgical system according to claim 11, wherein the at least one electrical sensor is configured to measure at least one energy property selected from the group consisting of tissue impedance, power, voltage, current, resistance, phase, and combinations thereof.

13. The electrosurgical system according to claim 12, wherein the generator includes at least one controller coupled to the at least one electrical sensor, the at least one controller configured to adjust output of the generator in response to the at least one energy property or the at least one tissue property.

14. The electrosurgical system according to claim 13, wherein the at least one controller is coupled to the at least one optical sensor, the at least one controller configured to adjust output of the generator in response to the at least one energy property or the at least one tissue property.

15. The electrosurgical system according to claim 11, wherein the at least one optical sensor is configured to measure at least one tissue property selected from the group consisting of transmittance, reflectance, translucency, opacity, hydrology, vascularity, thermal spread, tissue treatment depth, tissue seal quality, temperature, spectral content, and combinations thereof.

* * * * *